(12) United States Patent
Werringloer

(10) Patent No.: US 6,281,019 B1
(45) Date of Patent: *Aug. 28, 2001

(54) DEVICE FOR NON-PULSATING POST-COLUMN DERIVATIZATION

(76) Inventor: Jürgen Werringloer, Holunderstrasse 14, D-71083 Herrenberg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/214,790
(22) PCT Filed: Jul. 9, 1997
(86) PCT No.: PCT/EP97/03623
§ 371 Date: Apr. 5, 1999
§ 102(e) Date: Apr. 5, 1999
(87) PCT Pub. No.: WO98/02738
PCT Pub. Date: Jan. 22, 1998

(30) Foreign Application Priority Data

Jul. 12, 1996 (DE) .............................. 196 28 206

(51) Int. Cl.[7] .................................................. G01N 30/02
(52) U.S. Cl. ........................ 436/161; 422/70; 210/198.2; 210/656; 210/659
(58) Field of Search ............................. 436/161; 422/70; 73/61.56, 61.58; 210/198.2, 656, 659

(56) References Cited

U.S. PATENT DOCUMENTS

| | | | |
|---|---|---|---|
| 3,917,531 | * | 11/1975 | Magnessen . |
| 4,448,691 | | 5/1984 | Davis . |
| 4,474,664 | * | 10/1984 | Stevens et al. . |
| 4,549,965 | * | 10/1985 | Davis . |
| 5,305,658 | * | 4/1994 | Magee, Jr. . |
| 5,310,463 | | 5/1994 | Dadoo et al. . |

FOREIGN PATENT DOCUMENTS

| | | |
|---|---|---|
| 32770 | 7/1981 | (EP) . |
| 356 160 | 2/1990 | (EP) . |

* cited by examiner

*Primary Examiner*—W. L. Walker
*Assistant Examiner*—David Sorkin
(74) *Attorney, Agent, or Firm*—Pillsbury Winthrop LLP

(57) ABSTRACT

A device for performing a post-column derivatization in connection with liquid chromatography includes a separating column, a detector, an eluent withdrawal unit, connected to an outlet of the separating column, that withdraws eluents from the separating column, a reagent supply unit, arranged between the outlet of the separating column and an inlet of the detector, that supplies reagents to the eluents withdrawn from the separating column and a pump that simultaneously pumps eluents from the eluent withdrawal unit and pumps reagents to the reagent supply unit, wherein the pumping of reagents takes place free of pulsations.

16 Claims, 1 Drawing Sheet

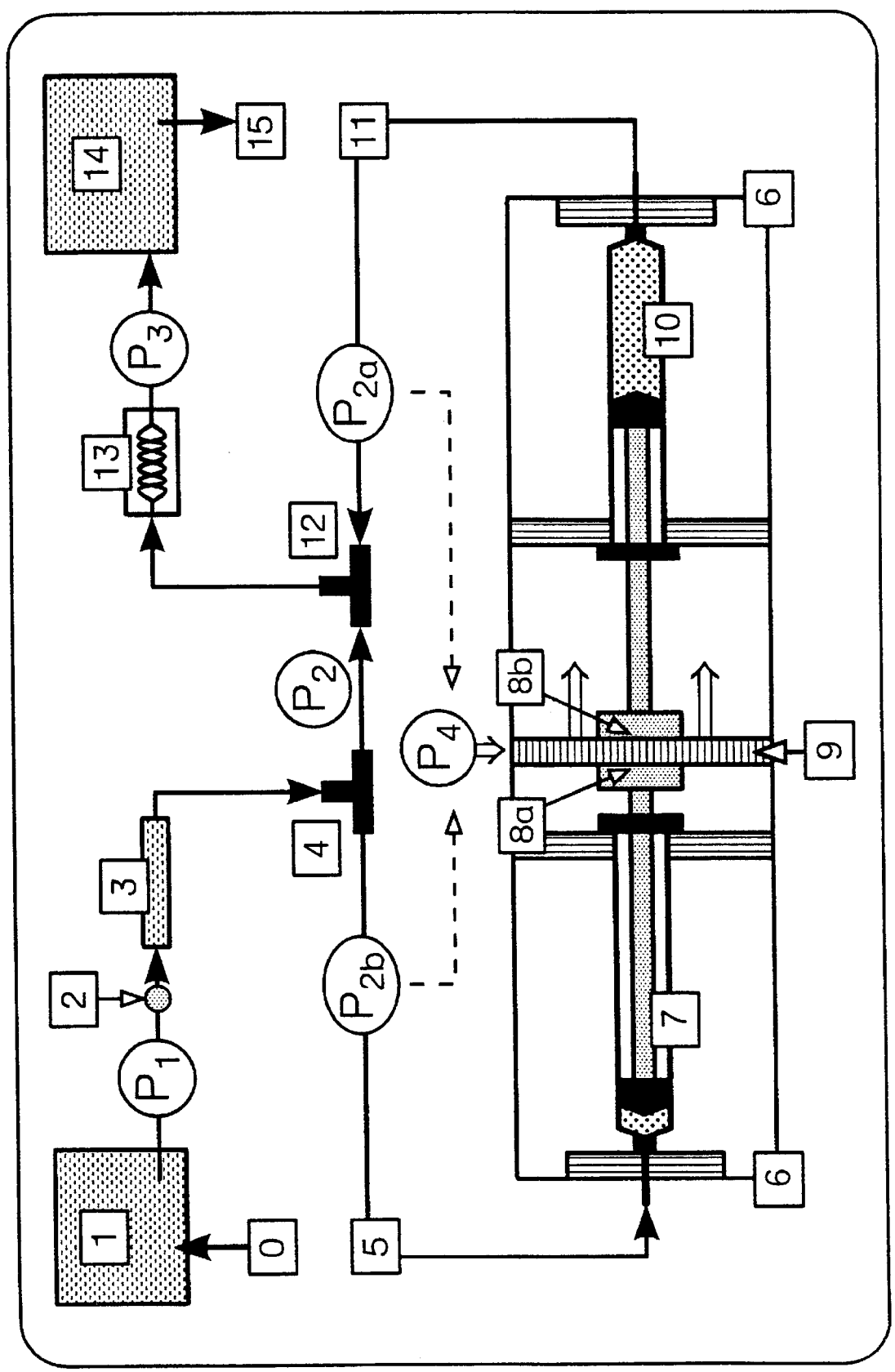

DEVICE FOR NON-PULSATING POST-COLUMN DERIVATIZATION

This application is the national phase of international application PCT/EP97/03623 filed Jul. 9, 1997 which designated the U.S.

BACKGROUND OF THE INVENTION

1. Field of the Invention

The invention concerns a device for the application of post-column (derivatization) reactions (PCR) in liquid chromatography using a universally applicable device for the pulsation-free addition of reagents.

2. Description of the Related Art

Liquid chromatography (LC) is a highly sophisticated analytical separation technique. In general this term is understood as High-performance (High-pressure) liquid chromatography (HPLC). Using high pressure the solutes of a sample are separated on a column filled with special materials of small particle size (stationary phase) using a liquid solvent as mobile phase. The small particle size results in a high number of theoretical plates per unit of column length and provides excellent conditions for the separation of the solutes. The resulting high cross-sectional resistance, however, requires the use of powerful pumps to provide the force to drive the mobile phase through the column. These pumps are designed to cause as little pulsation as possible of the mobile phase. The detection of the solutes separated is performed using various procedures such as UN/VIS-, fluorescence-, conductivity- or electrochemical-detections as well as radioactivity monitoring systems after supplementation of the mobile phase with a scintillation fluid for the determination of solutes labeled with radioactive isotopes.

The application of this methodology is limited, however, by the general weakness of the detection systems. Although the diversity of these systems appears to be enormous, the detection of very low concentrations of analytes, which are often encountered in HPLC-analysis, is possible only in the case of specific chromophores and fluorophores. In particular, some of the very important groups of substances like sugars, amino acids and steroids etc. escape detection at low concentrations. Further, the lack of a generally applicable detection system, like the FID in Gas Chromatography, can be considered as a general disadvantage of Liquid Chromatography as an analytical tool.

One of the answers to these problems is the application of chemical derivatization methods. These methods are based primarily on chemical reactions resulting in the conversion of the analytes into chromophores or fluorophores providing an amelioration of the sensitivity and, in addition, a high degree of specificity since only the compound of interest is derivatized. Because of these advantages chemical derivatization has found broad acceptance as an analytical tool in other areas of chromatography.

In principle, two options exist for the application of chemical derivatization in HPLC-analysis, i.e. derivatization of the analyte before application of the sample material to the column (pre-column derivatization) or derivatization of the analyte after its elution from the column (post-column derivatization). In most cases, depending on the specific analytical problem, only one of these methods can be applied. The pre-column derivatization is well known and in general use. One of the advantages of this procedure is the fact that additional pumps are not required; further, it allows long reaction times and it can be used, if reagent and derivative have similar light absorption properties. The disadvantages resulting from pre-column chemical derivatization are changes of the separation characteristics of the analyte and the tendency of artifact development.

In many situations, however, post-column derivatization—from now on called "PCR" (post-column reaction)—has to be applied. This procedure is used preferentially in the "on-line" mode. The only prerequisite for the application of PCR is that the chemical derivatization reactions can be carried out in a reproducible manner; i.e.—although favorable—the reactions do not even have to go to completion prior to reaching the detector system nor do they have to be defined chemically. The advantages offered by the PCR procedure in selectivity of reaction and specificity in the subsequent detection are won at the expense of the sensitivity of detection; i.e. the theoretically possible detection limits of the available detection systems worsen under PCR-conditions by a more or less pronounced broadening of bands, which depends of the dimension and the quality of the PCR reactor used. The main cause of the loss of sensitivity is due, however, to a lack of stability of the background signal, which may cause a severe deterioration of the signal/noise ratio, the decisive criterion of the limits of analyte detection.

The various parameters, which are decisive determinants of the detection limit of a typical PCR analysis can summarized as follows:

1. The intensity of analytical signal
2. The noise of the detector (high frequency noise)
3. The stability of the background signal (low frequency noise)
   a, of the eluate
   b, of the mixture of eluate and reagent Parameters 1, 2 and 3a are relevant in principle in all processes of HPLC analytics, though the problems related to the instrumentation can be regarded as optimized to a great extent. Parameter 3b, however, is unique to PCR analysis and represents until now an unresolved problem restricting the use and the potential advantages of PCR systems in a serious manner.

A variety of methods were proposed, therefore, to improve the handling of reagent addition. Reagents, for example, were introduced into the eluate using porous hollow fiber membranes, permitting the diffusion of the molecules required for the derivatization of the analyte (U.S. Pat. No. 4,448,691). This method, however, is not universally applicable; it can be used only under some very special circumstances. Customary, in contrast, is the use of pumps infusing the reagent into the effluent of the column via a special mixing device. In most cases only a reduced pulsation rather than a pulsation-free addition of the reagent is possible resulting in a substantial increase of the background noise. The extent of the pulsation-related noise depends on the intensity of the detector specific signal properties of the reagent/eluate mixture as well as on the difference of their individual signal intensities. It follows that the detection limit deteriorates with increasing intensity of the background signal of the fluid reaching the detector resulting in an amplification of the low frequency noise caused by the pulsations of the pump used to infuse the reagent.

The reason for the customary use of HPLC pumps with low pulsation properties is the fact that the infusion of the reagent into the small-diameter capillaries carrying the effluent from the column to the detector requires substantial forces because of the high internal pressure of the system. This pressure cannot be overcome by normal commercially available pulsation-free pumps; this is relevant in particular, if—as necessary in most instances—post-column reactors, further increasing internal resistance, are used to extend reaction times in order to optimize the derivatization reaction. An additional disadvantage of the standard HPLC-pumps is that their pulsating properties are optimized for flow rates which are substantially higher than those required for the infusion of the reagent; furthermore, not all parts of these pumps being exposed to the reagent fluid are chemically resistant to its various components.

Frequently it is attempted to smooth pulsations by insertion of conventional pulse dampers. This, however, is not very effective, because these dampers are designed to reduce pulsations under conditions of extremely high pressure, i.e. prior to entry of the mobile phase into the analytical column.

Pulsation-free syringe pumps, on the other hand, equipped with either high frequency stepping or synchronized motors, can be used for PCR purposes only under very few special circumstances, i.e. unusually low systemic pressure combined with a low demand for reagent fluid, thus allowing the use of small diameter syringes. Syringes, however, providing sufficient volume for universal PCR application and full-time (8 h) operation must have large plunger diameters and, hence, require the buildup of high linear forces; neither the performance of the motors nor the mechanical properties of the transmission devices of such syringe pumps are able to overcome the systemic pressure under these circumstances or, alternatively, are damaged irreversibly after only a short period of time.

In conclusion, there is a demand for a generally applicable device to carry out post-column derivatizations in HPLC analytics permitting a pulsation-free supplementation of the column effluent with the necessary reagents even if pressures at the point of entry to the HPLC capillary system exceed 10 bar (1 MPa). This device should be able to operated full-time (8 h working day); it should be simple in its construction, easy to handle, reliable and economic in its operation and reasonably priced.

SUMMARY OF THE INVENTION

The invention is based on a pressure equalizing withdrawal/infusion principle. A pulsation-free infusion of reagent by application of pulsation-free infusion pumps is made possibel when the pressure on the plunger of the infusion syringe is neutralized by an equal counter pressure, such that the pump has to overcome solely the frictional resistance of the plunger in the syringe cylinder and of the reagent in the capillary guiding the reagent into the HPLC system. Such conditions are generated by parallel withdrawing and infusion of liquid and reagent, respectively, using a pair of syringes in a manner generating equal pressure in both of these syringes, i.e. positioning the sites of the withdrawal unit and of the infusion/mixing unit in the HPLC capillary system in close proximity, assuring virtually identical (systemic) pressure at both outlet and inlet sites, respectively.

In practice, two syringes are used and connected to a withdrawal unit and an infusion/mixing unit, respectively, which are positioned in sequence between the outlet of the separation column and the inlet of the detector system. Pressure equalization is achieved placing the plungers of the withdrawal syringe head-on to the plunger of the infusion/reagent syringe such that the outlets of both syringes are pointing in opposite directions and keeping the barrels of both syringes in a fixed position. Provided the diameters/surface areas of the plungers heads are of equal size then the force required to move the plungers in either direction is the same; thus, if the motor of the pump is not engaged, neither withdrawal of eluate nor addition of reagent will occur since both syringes are under equal pressure.

Under conditions of active reagent infusion there will be no change of the pressure in the HPLC capillary system. The force to be generated by the motor of the pump is limited to the force required to overcome the frictional resistance of the plunger in the syringe cylinder and of the reagent in the capillary guiding the reagent to the infusion/mixing unit. Since pressure equilibration between both syringes will occur automatically, the withdrawing unit will gather passively a volume corresponding to that of the reagent infused. No change in the overall flow rate of the system will occur; there will be only a replacement of a part of eluate by the reagent. The control of the volume of exchange between eluate and reagent per unit of time is regulated preferably by an electronic programming device.

The invention has further advantages:

1. Syringes of any dimension can be used, provided they are resistant to the pressures encountered. A syringe of 50 ml capacity, for example, is sufficient to carry out analyses continuously over an 8 hour period assuming an infusion rate of 0.1 ml/min of the reagent and a flow rate of 1 ml/min of the mobile phase in the HPLC capillary system.
2. Using suitable syringes, also aggressive reagents which may cause damage by corrosion in conventional HPLC pumps can be applied without any problem.
3. Furthermore, depending on the respective construction of the pump, various reagents can be introduced into the system either in parallel and/or sequentially using two or more pairs of syringes.

BRIEF DESCRIPTION OF THE DRAWINGS

The invention will now be described with reference to FIG. 1 which is a schematic illustration of a device for performing a post-column derivatization in connection with liquid chromatography according to the invention.

DETAILED DESCRIPTION OF EXEMPLARY EMBODIMENTS

Eluent (0) is pumped using an HPLC-pump (1) through a separation column (3) generating the pressure P1. Between HPLC-pump (1) and separation column (3) samples can be applied to the system using an injection port (2).

The proposed device includes a withdrawal unit (4) connected to a withdrawal tube (5), which leads to a pressure equalizing syringe pump (6). Fixed to this pump (6) is a withdrawal syringe (2) for the collection of the eluent withdrawn. The plunger (8a) is positioned head-on to the plunger (8b) of the regent/infusion syringe (10) such that the eoutlets of both syringes are pointing in opposite directions. The pumping drive (9) remains in position since the pressure ($P_{2b}$) resting on the withdrawal syringe (7) is equal to the pressure ($P_{2a}$) resting on the reagent/infusion syringe (10). This resting pressure corresponds to the pressure ($P_2$) at the location of the withdrawal unit (4) and a reagent supply unit (12), respectively; hence, the pressure P4 ($=P_{2a}-P_{2b}$) equals zero.

Infusion of reagent is carried out by pulsation-free movement of the pumping drive (9), which has to overcome only the frictional resistance of the plunger (8b) and of the reagent in the supply tube, or capillary (11) guiding the reagent to the reagent supply unit (12). As a consequence of the automatic/passive pressure equilibration between both syringes corresponding volumes of eluent are withdrawn simultaneously at the withdrawing unit (4), and guided through the withdrawal tube (5) into the withdrawal syringe (7). As is required in most instances of post-column derivatizations a post-column reactor (13) can be applied, to extend reaction times in order to optimize the derivatization reaction. Leaving the reactor, the effluent is guided through a detector system (14) and then can be wasted (15), as done in most cases.

What is claimed is:

1. A device for performing a post-column derivatization in connection with liquid chromatography, comprising:

a separating column;

a detector;

an eluent withdrawal unit, connected to an outlet of the separating column, that withdraws eluents from the separating column;

a reagent supply unit, arranged between the outlet of the separating column and an inlet of the detector, that supplies reagents to the eluents withdrawn from the separating column;

a pump that simultaneously pumps eluents from the eluent withdrawal unit and pumps reagents to the reagent supply unit, wherein the pumping of reagents takes place free of pulsations;

at least one eluent syringe, connected to the eluent withdrawal unit and the pump by a withdrawal tube, that collects eluents pumped from the eluent withdrawal unit; and at least one reagent syringe, connected to the reagent supply unit and the pump by a supply tube, that supplies reagents pumped to the reagent supply unit, wherein the at least one eluent syringe and the at least one reagent syringe operate oppositely to one another and during pumping of reagents from the at least one reagent syringe to the reagent supply unit, the at least on eluent syringe is passively filled with eluents from the eluent withdrawal unit.

2. The device according to claim 1, wherein the at least one reagent syringe has a volume of at least 50 ml and addition of 0.1 ml/minute of reagent to 1 ml/minute of eluent allows continuous operation of the device for at least eight hours.

3. The device according to claim 1, further comprising a pump drive that drives the pump.

4. The device according to claim 3, wherein the pump drive is electronically controlled.

5. The device according to claim 1, further comprising a plurality of reagent syringes.

6. The device according to claim 5, wherein the plurality of reagent syringes are arranged in parallel.

7. The device according to claim 5, wherein the plurality of reagent syringes are arranged sequentially.

8. The device according to claim 1, wherein a volume of eluents pumped from the eluent withdrawal unit equals a volume of reagents pumped to the reagent supply unit.

9. The device according to claim 1, wherein the at least one eluent syringe includes a plunger and the at least one reagent syringe includes a plunger, and the pressure on the plunger of the at least one eluent syringe from the eluents is equal to the pressure on the plunger of the at least one reagent syringe from the reagents.

10. A method of performing a post-column derivatization in the course of liquid chromatography, comprising:

utilizing the device of claim 1.

11. A method of performing pulsation-free reagent supply in connection with post-column derivatization in the course of liquid chromatography, comprising:

utilizing the device of claim 1.

12. A method of performing post-column derivatization in connection with liquid chromatography, comprising:

separating eluents in a separating column;

withdrawing the eluents from the separating column to an eluent withdrawal unit;

supplying reagents from a reagent supplying unit to the eluents withdrawn from the separating column;

simultaneously pumping eluents from the eluent withdrawal unit and pumping reagents to the reagent supply unit;

collecting the eluents pumped from the eluent withdrawal unit in at least one eluent syringe; and passively filling the at least one eluent syringe with eluents from the eluent withdrawal unit during pumping of reagents from at least one reagent syringe to the reagent supply unit.

13. The method according to claim 12, wherein the supplying of reagents to the eluents includes supplying 0.1 ml/minute of reagents to 1 ml/minute of eluents for at least 8 hours.

14. The method according to claim 12, wherein the pumping of reagents to the reagent supply unit includes pumping from a plurality of reagent syringes.

15. The method according to claim 14, wherein the plurality of reagent syringes are arranged in parallel.

16. The method according to claim 14, wherein the plurality of reagent syringes are arranged sequentially.

* * * * *